United States Patent [19]

Ryan

[11] Patent Number: 5,809,476
[45] Date of Patent: Sep. 15, 1998

[54] SYSTEM FOR CONVERTING MEDICAL INFORMATION INTO REPRESENTATIVE ABBREVIATED CODES WITH CORRECTION CAPABILITY

[76] Inventor: John Kevin Ryan, 19 Ohinerau Street, Remuera, Auckland, New Zealand

[21] Appl. No.: 408,603

[22] Filed: Mar. 23, 1995

[30]     Foreign Application Priority Data

Mar. 23, 1994  [NZ]   New Zealand ............................ 248751

[51] Int. Cl.$^6$ ................................................. G06F 159/00
[52] U.S. Cl. ...................................... 705/2; 704/9
[58] Field of Search ...................................... 395/202, 203, 395/204, 759, 751, 760; 705/2, 3, 4; 704/1, 9, 10

[56]              References Cited

U.S. PATENT DOCUMENTS

| 5,301,105 | 4/1994  | Cummings, Jr. . |
| 5,390,330 | 2/1995  | Talati . |
| 5,483,443 | 1/1996  | Milstein et al. . |
| 5,577,169 | 11/1996 | Prezioso . |

OTHER PUBLICATIONS

"Coding Lexicon", British Orthopaedic Association, The Read Clinical Classification, Trauma Volume, Appendix 1, pp. 1–4, 107, 288–295.

*Primary Examiner*—Robert A. Weinhardt
*Attorney, Agent, or Firm*—Jacobson, Price, Holman & Stern, PLLC

[57]              ABSTRACT

The present invention relates to a system for coding data. An example implementation is disclosed whereby the coding system is a computer program especially suited to analysing text input to the computer by for example a keyboard, optical character recognition or voice recognition. The data to be coded may, for example, comprise information relating to an event, item or operation. In the preferred form of the invention, the input data is text describing a medical diagnosis and operation which would be dictated or recorded by a surgeon subsequent to an operation being performed on a patient. The coding system of the present invention analyses each word or term of the medical information in conjunction with specialised and generalised dictionaries of words and terms, along with the relationships between individual words or terms. In this way, in addition to producing a compressed symbolic representation of the original information which may later be interrogated or used for statistical analysis, the present invention is also capable of correcting or supplementing the original information.

22 Claims, 5 Drawing Sheets

SYSTEM FOR CONVERTING MEDICAL INFORMATION INTO REPRESENTATIVE ABBREVIATED CODES WITH CORRECTION CAPABILITY

BACKGROUND OF THE INVENTION

1. Field of the Invention

This invention relates to coding systems and more particularly but not solely to coding algorithms which express ideas or information as codes for later use.

2. Description of the Prior Art

Most existing systems which express ideas or information as codes deal with limited information, for example, a name or a stock item. The connection between the code and the information is rigid and the method of assessing the data is uniform. In many industries and professions, however, this degree of uniformity is not present. In medicine, for example, there are tens of thousands of words which legitimately expressly subtly different concepts and numerous similes and similar sounding words with quite different meanings, while totally dissimilar phrases may express very similar information.

Existing systems which translate medical information (including diagnoses and operations) into computer codes include the World Health Organization's ICD9 system and the British READ system. ICD9 is a numeric coding system where diagnoses and/or operations are expressed as a floating point number. For example, "812.3" in the ICD9 system is a "Fracture of humerus" (upper arm bone). Systems which rely on the ICD9 coding system typically employ clerical coders to examine the clinical notes and then find the appropriate code which matches the information in the clinical notes.

The READ system uses an alphanumeric code, with combinations of letters and digits used to express the information. Unlike the ICD9 system, the READ system is hierarchical in that diagnoses and operations with increasing degrees of complexity retain the same stem part of the code with additional information added to the end. Clerical coders are commonly employed to manually translate surgeons' notes into the READ codes. The clerical coders achieve this by selecting words and similes from tables of commonly used terms which are also referenced to the appropriate codes. In both the ICD9 and READ systems there are many opportunities for errors to make their way into the coding system. For example, the coders are usually not highly trained in the field which they are coding and are, therefore, not uniformly reliable to the degree of accuracy required if medical decisions are to be made from the coded information.

Extraction or interrogation of information using existing coding systems also requires a sound knowledge of the subject. In existing medical coding systems, for example, very similar diagnoses may have totally dissimilar codes. An example is Rheumatoid arthritis which has ICD9 code 714 while Charcot's Arthritis has ICD9 code 250.6. A search through coded information for "arthritis" will, therefore, need to include all such widely varying codes. Similarly, "Monteggia's Fracture" is actually a combination of a fracture and a dislocation or subluxation. Therefore, any searches for "injured joints" will need to include Monteggia's fracture, Galeazzi fracture and a host of others whose names and codes give the reader no clue to their nature. This non-uniformity of codes requires a considerable degree of sophistication and vigilance by researchers.

SUMMARY OF THE INVENTION

It is, therefore, an object of the present invention to provide a coding system which goes some way towards overcoming the above disadvantages or which at least provides workers in the field with a useful choice.

Accordingly in one aspect the invention consists in a method of coding data in which codes are assigned to the data. The method comprises the steps of:

i) Dividing the data into sub-parts, each said sub-part being of a particular sub-part type.

ii) Preliminarily grouping the sub-parts into sub-groups by introducing divisions in the data. Each sub-part in a particular sub-group sharing an association with all other sub-parts in that particular sub-group.

iii) Examining each of the sub-group for completeness in regard to each sub-group containing a predetermined distribution of sub-part types.

iv) Completing the sub-groups by amending the constituent sub-parts so that each sub-group contains the predetermined distribution of sub-part types.

In a second aspect the invention consists in a program, for execution by a computer, which analyses input data describing an event, item or operation and produces coded output to represent the input data and also attempts to correct deficiencies in the data. The program comprises the steps of:

i) Dividing said input data into sub-parts, each sub-part being of a particular sub-part type.

ii) Preliminarily grouping the sub-parts into sub-groups by introducing divisions in the data. Each sub-part in a particular sub-group sharing an association with all other sub-parts in the particular sub-group.

iii) Checking each said sub-group for completeness in regard to each sub-group containing a predetermined distribution of sub-part types.

iv) Attempting to complete the sub-groups so that each sub-group contains the predetermined distribution of sub-part types by analysing the sub-groups in relation to each other and carrying out completion operations on the sub-parts and sub-groups.

The invention consists in the foregoing and also envisages constructions of which the following gives examples.

BRIEF DESCRIPTION OF THE DRAWINGS

One preferred form of the present invention will now be described with reference to the accompanying drawings in which.

DETAILED DESCRIPTION OF THE PREFERRED EMBODIMENT

Broad Overview

Figure 1:
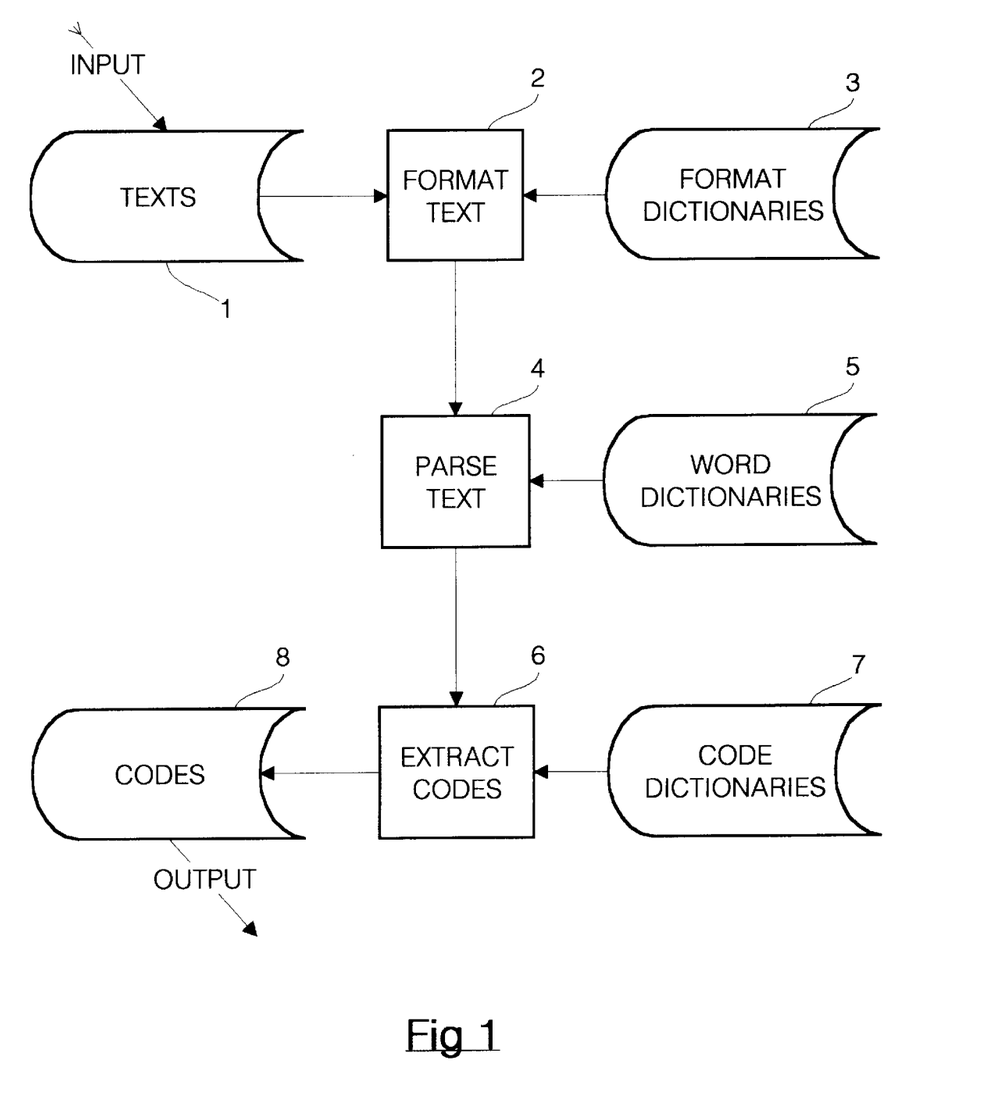
FIG. 1 is a flow diagram showing a broad overview of the coding algorithm of the present invention.

In the figures each rectangular block represents an algorithm. With reference to FIG. 1, a flow diagram broadly illustrating the method of coding of the present invention is shown. The flow diagram of FIG. 1 may be, for example, carried out in the execution of a computer program. An example of a high level computer language which may be used to write a program to facilitate execution of the coding system of the present invention is Microsoft Corporation's FoxPro programming language and database software package.

It can be seen in FIG. 1 that text, for example surgeon's notes regarding diagnoses and operations, is input to the flow diagram or program at block 1. The process of inputting the text may be by way of a typist, typing a surgeon's dictated notes subsequent to an operation or may be derived from optically scanned documents in which case Optical Character Recognition (OCR) could be used. Alternatively a voice recognition system may be used to directly translate the surgeon's verbally dictated or taped notes. At block 2 this input text is formatted whereby most punctuation marks and plural or tense modifiers are removed.

In order to assist in formatting the input text, format dictionaries at block 3 are perused to compare each word being formatted to a list of words in the dictionaries. Alternatively, the step of formatting could be omitted and instead, words with plural or tense suffixes, for example, could be included in resultant broader format dictionaries. Once the text has been formatted it is passed to block 4 in which the bulk of analysis of the text is carried out in association with word dictionaries at block 5 which contain tables of words which may be compared to the words being analysed at block 4.

Each of the aforementioned dictionaries contains words of a certain type, for example, the anatomical dictionary contain words pertaining to the anatomy. It should, however, be noted that although the coding system is to be described with reference to a number of individual dictionaries, one large dictionary could be used which contains all necessary words along with other related information on the words. Where one or more dictionary is grouped together, there will also be included a flag or field or other method of distinguishing one databases' records from another.

In block 4, the formatted text is parsed wherein each word or phrase of the input text is expressed symbolically in the form of an indicative code or sub-part called a "code snippet". Eventually, the code snippets may be altered, depending on the rest of the words in the sentence or clause. The code-snippets are grouped into sub-groups or "clusters" representing a sentence, phrase or clause in the input text. The code snippets are manipulated by the algorithms of the present invention then stored or output as representative codes in, for example, a database for later interrogation or statistical analysis.

Parsing

Figure 2:
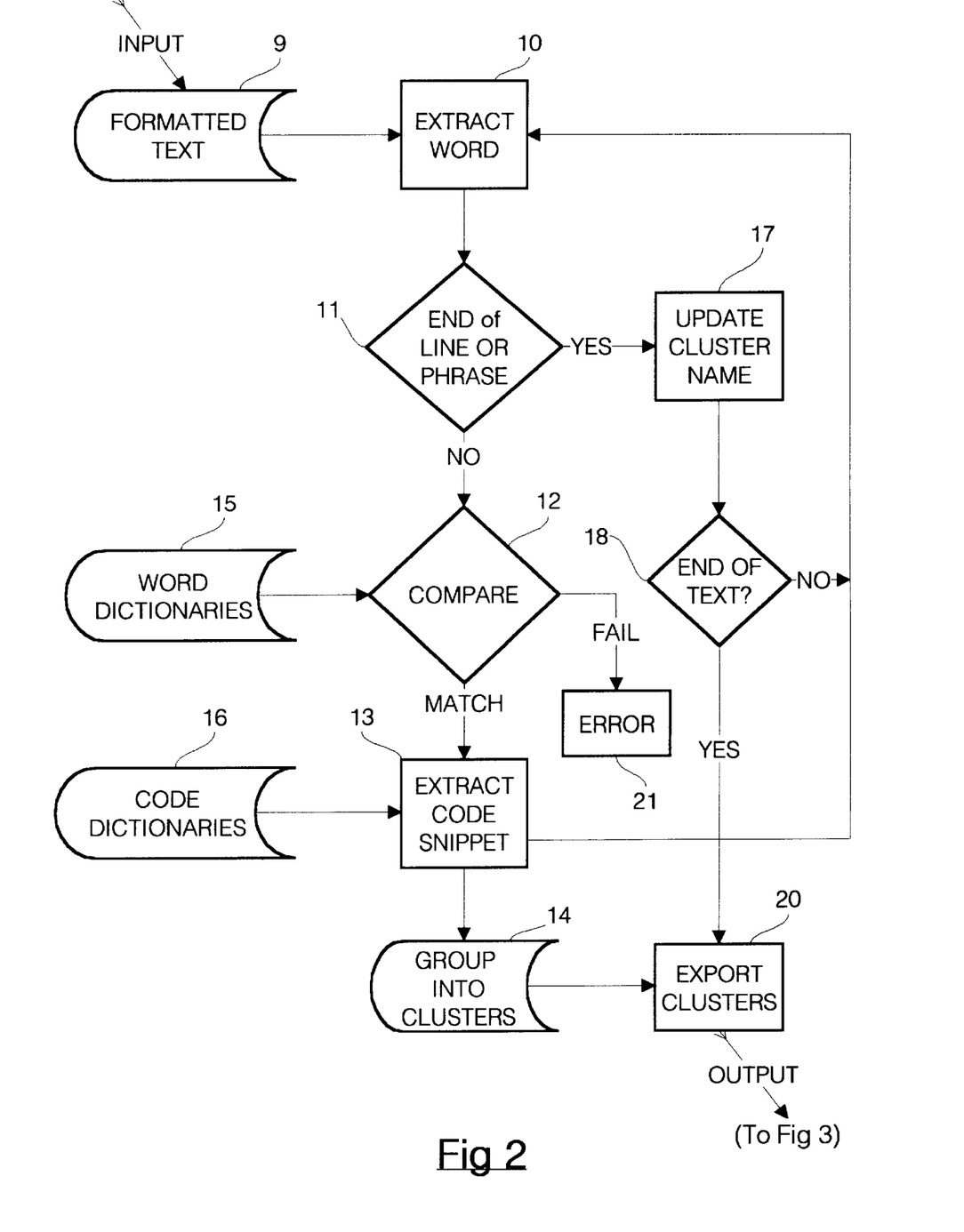
FIG. 2 and FIG. 3 are consecutive flow diagrams, detailing the coding system of FIG. 1.
Figure 3:
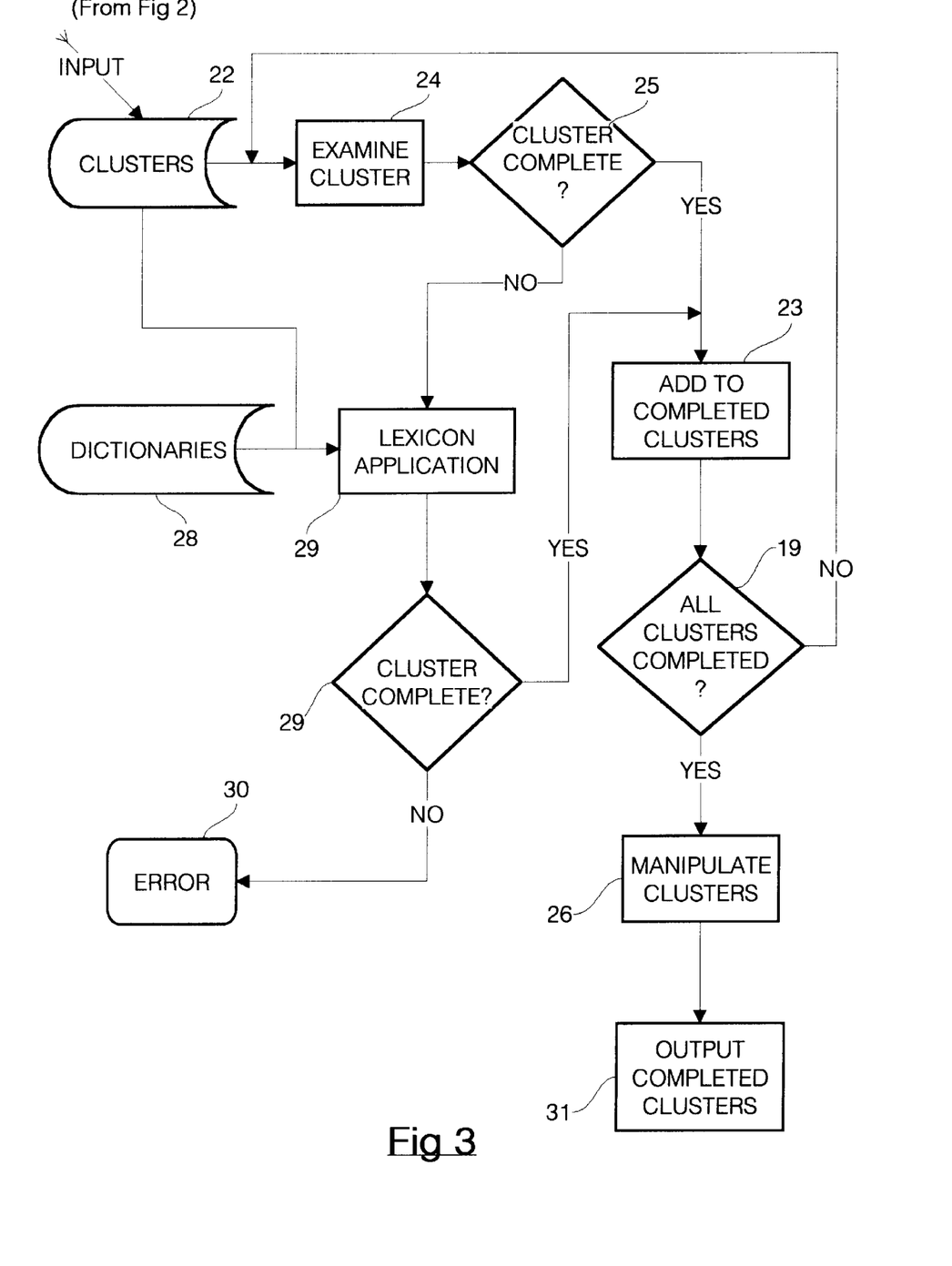

With reference now to FIGS. 2 and 3, the parsing block 4 of FIG. 1 will now be explained in more detail.

At block 9 the text formatted at block 2 of FIG. 1 which has been stripped of punctuation marks and plural or ten modifiers, is input to block 10 as uniformly formatted text. At block 10, starting from the beginning of the text, a word is sequentially "peeled" from the string of formatted input text and compared to dictionaries of words and similes. In this specification, "words" which are "peeled" from the text or stored in dictionaries may be single words or may be group of words or phrases with associated meaning. For example, in medicine, "greater Trochanter" or "junction of upper and middle" may be stored as words in the dictionary as these are commonly used medical phrases. The dictionaries may be contained in one or more arrays or database files or tables or other mode of data expression. In the case of medicine, there may be, for example, one or more dictionaries for diagnosis, for operations, for anatomic areas and for conjunctives, other special words, numbers, fractions and other numerically expressed information including, but not limited, to percentages, degrees, grades, stages and other descriptions. Similar comparison dictionaries are required for different source text languages and for code conversion to other systems, including but not limited to the World Health Organization's ICD9 System and the British READ System.

As the words are parsed, they are compared to words in the dictionaries. When the current word is found, the dictionary entry may contain a flag for further manipulation of the word or even a repeat search. For example, "#", which is a medical abbreviation for "fracture" would be found and converted to "Fracture" before a re-search. This usually happens with similes but also happens with numbers, for example, "Three hundred" would extract the "three" as 3 and the "hundred" as the action of multiplication by 100, yielding 300. Similar rules apply to numbers like "thirty five" where the five has to be added to the 30, yielding 35. Numbers are also affected by words like "percent", "degree" and so on.

As the words or phrases are extracted from the formatted text, a check is made at block 11 to determine whether the end of the line of input text has been reached. If the end of the line has not been reached, then control passes to block 12 wherein the word or phrase is compared to the words in the word dictionaries at block 15. If the word or phrase does not match up with an entry in the word dictionaries, then a match has not been made and, typically, an error message is generated at block 21 for the author of the text or other designated person's notice so that the text may be corrected, re-input and correctly matched. Alternatively, frequently unmatched words may be entered as new records in a dictionary.

If, however, the word is matched to a data record held in the word dictionaries then control passes to block 13 where code snippets, extracted from the dictionary, are used to represent the matched word from the formatted text. A parsing table, which contains the code snippets derived from the input words, grouped into initial clusters, along with further code information from the dictionaries is produced at block 14. Typically, this further information includes a description of the word type (for example, in medicine, the word "Humerus" is identified as an anatomical entity while "shaft" is an anatomical modifier). This description is derived from the dictionary the in which the word was found in, for example, words from the "diagnosis" dictionary are diagnostic. It is also possible to have sub-descriptive words and modifiers.

In addition, a "cluster name", referring to the cluster of code snippets and associated information belonging to each code snippet is associated with the snippet. Code snippets in the same phrase will be placed in the same cluster while code snippets from the next phrase will be placed in their own separate cluster. The code snippets and associated information are saved in the aforementioned parsing table which may be a database, table, memory array or other alternative method of data storage. Once the code snippets have been extracted at block 13 they are initially grouped into clusters at block 14 before control returns to block 10 and the next word is extracted from the formatted text.

It the end of a line or phrase (rather than the next word) is detected at block 11, then cluster name is updated at block 17 and a decision is made at block 18 to determine whether or not the end of text has been detected. Phrases usually end with words like "and", commas or can be forced to end by a change of meaning, for example, in medicine, a midsentence change from an operation to a diagnosis. Lines usually end with carriage returns, line feeds or both. During parsing, a cumulative description of parsed words is maintained in a memory able or by some alternative method. A less satisfactory alternative method is to re-examine the snippets at a later stage to determine the contents of each cluster. In any case, as each cluster is finished, the cluster name along with the accumulated word descriptions is saved into a database, memory array or some other form of storage. The cluster names are unique for each phrase and they are affected by the reason why the cluster ended. Because of this, the reason for the cluster ending is also saved.

Once all the text has been parsed, the parsing table at block 14 contains code snippets aggregated into clusters by the cluster names. Stored information about the descriptions of words in each cluster will also be available in the parsing table or elsewhere.

If the end of the input text has not been detected at block 18 then the next line or phrase of text must be sequentially analysed and, therefore, control returns to block 10. If, however, the end of text has been reached at block 18, control then passes to block 20 at which point the accrued clusters in the parsing table at block 14 are exported to block 32 of FIG. 3. It should be noted that alternatively, all snippets could be determined, saved in a table and then cluster groupings could be decided once all the snippets have been determined.

Creating and Completing Clusters

With reference now to FIG. 3, clusters from block 20 of FIG. 2 are input to block 22 as, for example, the previously described parsing table. Starting from the last snippet in the parsing table and working back toward the start of the parsing table, clusters are examined at block 24 with the aid of dictionaries at block 28 and may contain any number of code snippets with each snippet's associated information.

A complete cluster should contain a complete idea or piece of information such that the snippets' descriptions fall into a set of predetermined categories. In the case of medicine, each cluster should contain at least one "clinical" snippet (for example a diagnosis or operation), an anatomical area snippet (for example "femur") and the side in question. Clinical and anatomical sub-expressions or modifiers may also be present but have no impact on cluster completeness. An example of a typical completed cluster could be "Spiral Fracture Right Humerus" as it contains a clinical snippet "fracture", an anatomical snippet "humerus" and the side. This cluster also contains a clinical modifier "spiral" which has no impact on completeness but describes the type of fracture, however, "spiral fracture" or "humerus" alone is incomplete.

At block 25 a decision is made as to whether or not the present cluster is complete. If the cluster is found to possess the necessary snippet types then the cluster is added to a temporary store of completed clusters at block 23. This temporary store may be the parsing table itself or it may be a separate table or array for example. At block 19, a decision is made to determine whether or not all of the clusters in the parsing table have been examined. If more clusters are to be examined, then control passes back to block 24. If all clusters have been examined, then control passes to block 26 wherein the clusters undergo a series of manipulations to prepare them for export. The manipulations include, in no specific order:

i) sides are applied, if side is not specified in the cluster, ii) anatomical modifiers are applied to anatomical snippets, iii) clinical modifiers are applied to clinical snippets, iv) numbers and numeric expressions (for example, percentages) are applied, v) redundant information is removed, for example, in medicine, "Greater Trochanter" invariably refers to part of the femur bone. The word "femur" may nevertheless accompany "Greater Trochanter" in the source text and, therefore, "femur" is eliminated from the coded information, and vi) clinical, anatomical and side information is joined into a record.

When these manipulations have been carried out, the complete formatted code clusters are exported or output at block 31 of FIG. 3, completing the coding process of the present invention.

Figure 4:
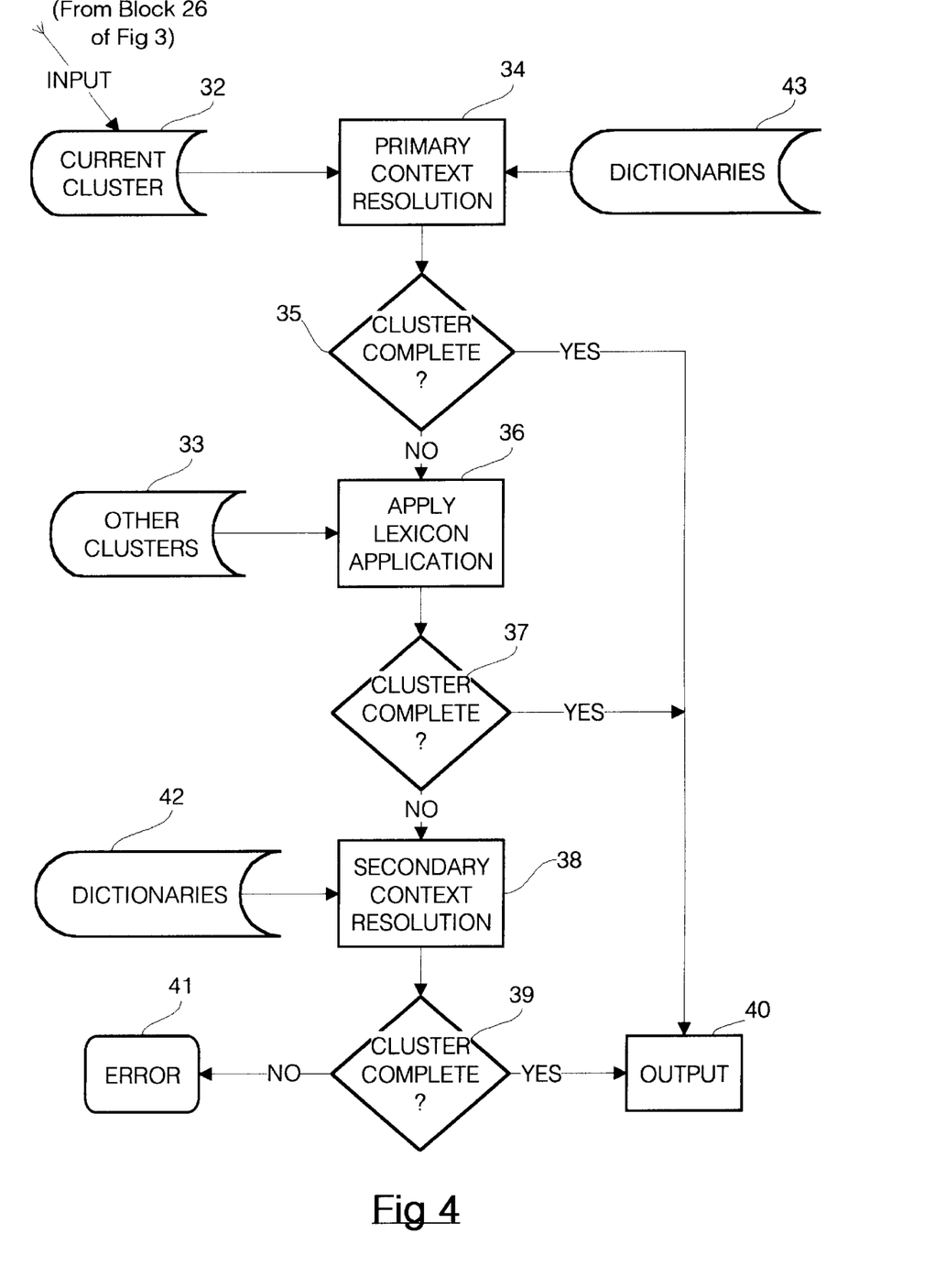
FIG. 4 is a flow diagram expanding on the Lexicon application block of the flow diagram of FIG. 3.

If at block 25 the present cluster is found to be incomplete, then a "Lexicon Application" method, which will sow be explained with reference to FIG. 4, is carried out on the incomplete cluster with the aid of dictionaries at block 28.

Once the Lexicon Application is completed a final check as to the cluster's completeness is carried out at decision block 29. If the cluster is still not complete then an error message is generated at block 30, typically alerting the author of the cluster or some other designated person so that the cluster may be corrected and re-input. If the cluster has been made complete by the Lexicon Application, then from block 29, control will pass to block 23 and the cluster will be added to the temporary store of completed clusters for eventual manipulation and output.

Lexicon Application Method

With reference to FIG. 4 the Lexicon Application block 27 of FIG. 3 will now be described.

The Lexicon Application method involves examining certain snippets to determine their meaning in the context of the surrounding snippets. This will usually, but not necessarily, involve the aforementioned indicative codes stored with each parsed word to describe the completeness of information during parsing, as well as the indicative code to describe the reason why each clause was terminated. This is because a clause which terminated with a comma requires a different Lexicon Application response from that of a clause which terminated with, for example, a full stop, or the word "and" or "with".

In addition to the Lexicon response, certain words require reanalysis to express their meanings in context. For example, in medicine the word "head" may refer to part of a bone or muscle anywhere in the body in addition to its usual meaning of the uppermost part of the body. This reference is determined by the information accompanying the word "head" in the surrounding source text. Such words are identified either in the initial parsing process or subsequently and compared to surrounding information by the Lexicon Application's context resolver algorithm, program, procedure, table, array or other method to interpret the word in context.

The Lexicon Application method involves several steps. Before checking for completeness at all, a primary context resolution is performed. This is carried out at block 34 with a relatively high degree of specificity. In block 34 the context of the current cluster is analysed with the assistance of dictionaries at block 43. In the previous example, using the snippet "head", the primary context resolution would determine the meaning of "head" in context. By including the word "muscle" or a type of bone with the snippet a different snippet and description would result. This alone may complete a cluster.

If the cluster is still incomplete, the Lexicon Application at block 36 is applied which examines the surrounding clusters, attempting to extract the missing information from them. For example, the sentence "Fracture of Humerus and Ulna" would yield two clusters, the second cluster (after the "and") is incomplete. The Lexicon Application recognizes that the second cluster's missing clinical item ("fracture") can be appropriately extracted or copied from the first cluster because the words on either side of the word "and" are of the same general type. This is an example of a Lexicon Application rule. Similar rules govern various other situations. Block 36 has a set of values which determine how information is exchanged between adjacent clusters and, as depicted by block 33, this exchange of information is not limited to directly adjacent clusters but may serve to transport information to clusters further afield within the formatted text.

At block 37, the cluster is once again checked for completeness and in the case where it is not complete, control is passed to block 38. At block 38 a secondary context resolution is performed. This time, the specificity of resolution is far less. For example, the snippet for the word "head" would be applied by the primary context resolution to a muscle or a bone. In the secondary context resolution, "head" would be applied to a muscle or bone if one has been extracted by Lexicon Application. Otherwise the snippet for "the head" would be produced providing an anatomical snippet and usually completing the cluster. "The Head" cannot be assumed in the primary context resolution because Lexicon Application may provide a muscle or bone to apply "head" to.

Dictionaries 42 are associated with the second context resolution block 38 and may be the same dictionaries used at block 43. If the cluster can not be completed or the context can not be determined at block 38 (which may be the same as block 30 of FIG. 3), typically an error message is generated for the text author or other designated persons notice so that the cluster may be corrected and re-input.

If, however, all clusters are complete at block 35 or block 39, control returns to block 29 of FIG. 3.

EXAMPLE

Figure 5:
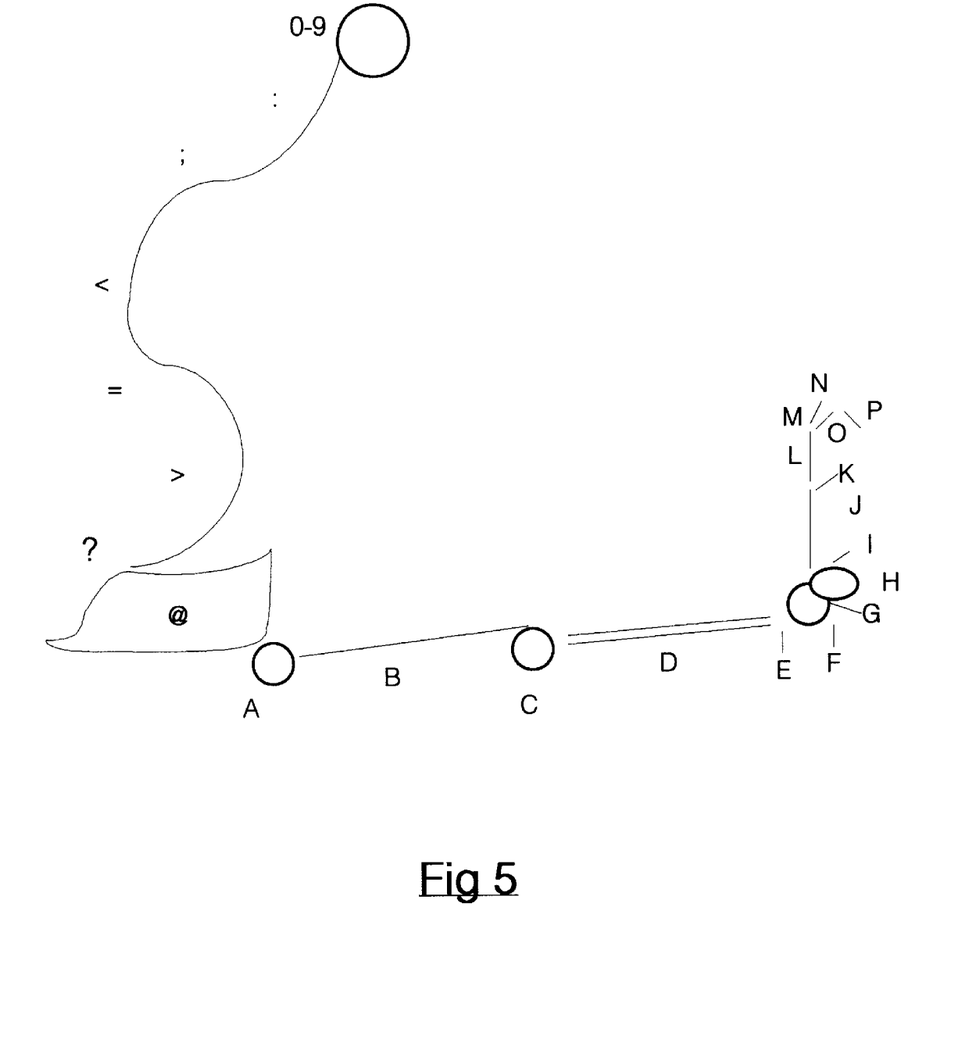
FIG. 5 is a highly stylized diagram of a human with areas of the body represented by example code snippets used in the flow diagram of FIG. 1.

An example of the coding method of the present invention as applied to the medical clinical notes will now be displayed with reference to FIG. 5. FIG. 5 is a homonculus (highly stylised picture of a human) which includes example code snippets referencing various areas of the body, (for example 0–9 refer to features of the human head while A–Z refer to features of the human leg, A being the hip, L, M, N, 0, P the bones and joints of the toes).

The following is a sample of text which, as has previously been explained, may have originated from a surgeon's dictated notes:

"Diagnosis: Spiral Fracture upper third left tibial shaft and middle third fibular shaft Operation: Tibial Nail left side"

The following are excerpts from three separate dictionary entries, which as has also previously been mentioned, may alternatively be incorporated in one dictionary:

| Diagnosis Dictionary | Operation Dictionary | Anatomical Dictionary |
|---|---|---|
| ! Fracture | Z Nail | ~D1 Tibia |
| X Spiral |  | ~D2 Fibular |
|  |  | A Shaft |
|  |  | 0 Upper third |
|  |  | 1 Middle third |

It should be noted that the positioning of these characters (for example the number of leading spaces) is deliberate and highly significant as this may, for example, indicate the type of word (for example the area of the body).

The Text is input to the coding system at block 1 of FIG. 1 and formatted at block 2. As this text contains no unnecessary information (including tense or plural suffixes) it is then parsed at block 4. The following is a representation of the parsing table produced from the example input text.

Parsing Table

| Snippet | Type of Snippet | Cluster Name | Cluster Type |
|---|---|---|---|
| X | Diag modifier | A | Diag |
| ! | Diag | A | Diag |
| 0 | Anat modifier | A | Diag |
| ~D1 | Anat | A | Diag |
| A | Anat modifier | A | Diag |
| 1 | Anat modifier | B | Diag |
| ~D2 | Anat | B | Diag |
| A | Anat modifier | B | Diag |
| ~D1 | Anat | C | Oper |
| Z | Operation | C | Oper |

It can be seen that three clusters have been formed being clusters A, B and C. Cluster A is derived from "spiral fracture upper third left tibial shaft", cluster B derived from "middle third fibular shaft" and cluster C derived from "Tibial Nail left side".

In the parsing table, clusters A and C are complete as they have both clinical and anatomical snippets and an associated side ("left side"), this side is noted for both clusters. Therefore, at block 25 of FIG. 3, both clusters A and C would be transferred to block 23 and temporarily stored. Cluster B, however, is incomplete and would progress to block 27 for lexicon application. As the last word in cluster A ("shaft") and the first word in cluster B ("middle third") are of the same general type (Anatomical modifiers), then cluster B's missing clinical item(s) may be copied from cluster A. Thus, the lexicon application copies the snippets "spiral" and "Fracture" into cluster B. Also, as cluster B is missing a side, this is extracted from the "left side" noted for clusters A and C.

The completed clusters are then manipulated at block 26 where the modifier snippets are applied and the completed representative codes shown below are produced for output.

| Diag cluster | !X | (L) | ~D1A0 |
|---|---|---|---|
|  | !X | (L) | ~D2A1 |
| Oper Cluster | Z | (L) | ~D1 |

ADVANTAGES

Thus it can be seen that the present invention, by keeping dictionaries of, for example, medical information, is able to interpret and when necessary modify input data. The advantages of the present invention include its speed of operation, its ability to code text impartially and reproducibly and its overall accuracy.

All diagnoses or clinical entries involving a particular area will generate exactly the same character in the area position of the code snippet. Thus, interrogating for injuries or events involving that area simply requires a search for the relevant code snippet embedded within the code. More importantly, the codes are grouped so that information can be derived from the placement and nature of the snippet contents. For example, all snippets with the letters A–Z at the area position are in a limb with upper case letters (A–Z) representing the leg and lower case letters (a–z) representing the arm (not shown). It should be noted that there is a correlation between the parts of the arm and leg, for example, the hip (A) corresponds to the shoulder (a).

To search for limbs, one simply searches for codes with letters at the area position. The areas adjacent to any area are one below and one above the ANSI representation of the current area. This allows meaningful groupings in interrogation. For example, the joints of any long bone will have snippets one below and one above the bone's own area snippet. For the bone of the thigh (the femur) the joints are A (the hip) and C (the knee). These snippets can be further refined by modifiers like proximal, distal, medial lateral and anterior. Such modifiers have stereotyped snippets and during the process described they will be applied to the area snippet. "Lateral thigh" might be expressed as Bx and "Anterolateral thigh" as Bxy where x and y are snippets for lateral and anterior respectively.

Similar stereotyped snippets exist for bones, muscles, soft tissues and other parts of the body. For example, regarding the "femur" (bone of the thigh), if the snippet for "long bone" is "!" and the snippet for joint is "@" then "femur at the knee" might be expressed as "!B@C". This includes a surprising amount of information as we are not only discussing a bone but it is a long bone, associated with the thigh, and we are describing one of its joint surfaces, the distal one, which is at the knee joint. Interrogation involving any of these elements need only specify a pattern to which the codes must adhere. For example, injuries involving the knee joint all have "@C" at the defined position in the code while femur always starts with "!B" whether we are referring to the hip, the thigh or the knee.

Although the method of coding of the present invention has been described with reference to the coding of surgical data it is also applicable to other data using dictionaries appropriate to the application giving rise to the data. Also, it is obvious that the code snippets used in the example could be any characters or symbols other than those shown.

I claim:

1. A method of coding data representing diagnoses and/or operations which is carried out by a computer in which representative codes are assigned to said data comprising the steps of:
   i) inputting said data to said computer,
   ii) dividing said data into sub-parts, each said sub-part being of a particular sub-part type,
   iii) preliminarily grouping said sub-parts into sub-groups by introducing divisions between some sub-parts in said data, each sub-part in a particular sub-group sharing an association with all other sub-parts in said particular sub-group,
   iv) examining each said sub-group for completeness in regard to each sub-group containing a predetermined distribution of sub-part types,
   v) if the examination of step (iv) reveals that the sub-group is not complete, completing said sub-groups by amending the constituent sub-parts so that each sub-group contains said predetermined distribution of sub-part types, and
   vi) outputting said completed sub-groups as coded data for later interrogation or analysis.

2. A method of coding data as claimed in claim 1 wherein at least one list of records is provided and said data is a sequential stream of text and wherein said step of dividing said data into sub-parts comprises parsing said data whereby each word, or group of words, of said text is differentiated by comparing each said sub-part to records in said at least one list of records, said at least one list of records also indicating the type of records in said list.

3. A method of coding data as claimed in claim 2 wherein said step of dividing said data into sub-parts includes the step of associating the name of said list of records which contained the sub-part with the sub-part.

4. A method of coding data as claimed in claim 2 wherein said step of preliminarily grouping said sub-parts into sub-groups comprises the steps of:
   i) comparing each said sub-part to records in said at least one list of records, said at least one list of records also indicating the type of records in the list, and
   ii) representing each sub-part by a related record in said list or by an associated related record if the sub-part matches a record in one of said lists.

5. A method of coding data as claimed in claim 2 wherein said step of completing said sub-groups comprises the steps of:
   i) carrying out a first examination of any sub-parts which may have a dual meaning in order to determine their appropriate meaning in the context of the surrounding sub-parts and inserting associated records from said at least one list of records to alter said sub-part or sub-group,
   ii) examining the sub-groups adjacent each said sub-group in order to extract or copy sub-parts into an incomplete sub-group, and
   iii) carrying out a second examination of sub-parts which may have a dual meaning to determine their appropriate meaning in the context of the surrounding sub-parts and inserting records from said at least one list of records to alter said sub-part or sub-group.

6. A method of coding data as claimed in claim 2 wherein at least one of said at least one list of records comprise terms relating to medical applications, at least one of said at least one list of records comprises anatomical terms relating to common names or descriptions of the bodily structure, at least one of said at least one list of records comprises clinical terms relating to the treatment of patients, and at least one of said at least one list of records comprises terms relating to the position of said anatomical terms.

7. A method of coding data as claimed in claim 1 wherein said divisions are introduced into said data in order to group associated sub-parts together and the positioning of said divisions is determined by one of a predetermined set of reasons and said step of preliminarily grouping said sub-parts also includes keeping a record of the reason for the positioning of divisions between sub-groups and identifying the list in which each sub-part was found.

8. A method of coding data as claimed in claim 1 wherein said divisions are introduced into said data in order to group associated sub-parts together and the positioning of said divisions is determined by one of a predetermined set of reasons and symbolic indicative codes represent said sub-parts, and wherein said symbolic representative codes are stored in a table along with said sub-part type and said reason for the positioning of divisions between said sub-groups.

9. A method of coding data as claimed in claim 1 wherein said method also includes, for any sub-group which is in error and therefore unable to be completed during said step of completing, the step of outputting a message in order that the data corresponding to that incomplete sub-group may be re-input.

10. A method of coding data as claimed in claim 1 wherein said predetermined distribution of sub-types comprise a clinical sub-part, an anatomical sub-part and a sub-part relating to the position of said anatomical sub-part.

11. A method of coding data as claimed in claim 1 wherein said step of completing said sub-groups includes, for each sub-group, uniformly positioning said sub-parts within each said sub-group to facilitate efficient searching of said coded data wherein only the sub-part at a relevant position within said sub-group need be examined.

12. A computer programmed to analyze input data describing an event, item or operation and produce coded output to represent said input data and also attempts to correct deficiencies in said data, said program comprising:

i) means for inputting said data to said computer, ii) means for dividing said input data into sub-parts, each said sub-part being of a particular sub-part type, iii) means for preliminarily grouping said sub-parts into sub-groups by introducing divisions between some sub-parts in said data, each sub-part in a particular sub-group sharing an association with all other sub-parts in said particular sub-group, iv) means for checking each said sub-group for completeness in regard to each sub-group containing a predetermined distribution of sub-part types, v) means for determining if the means for checking reveals that the sub-group is not complete, and if not complete, for attempting to complete said sub-groups so that each sub-group contains said predetermined distribution of sub-part types by analyzing said sub-groups in relation to each other and carrying out completion operations on said sub-parts and sub-groups, and vi) means for outputting said completed sub-groups as coded data for later interrogation or analysis.

13. A computer programmed according to claim 12 wherein at least one list of records is provided and said means for dividing said data into sub-parts comprises means for parsing said data whereby each word or phrase of said text is differentiated by comparing each said sub-part to records in said at least one list of records, said at least one list of records also indicating the type of records in said list.

14. A computer programmed according to claim 13 wherein said means for dividing said data into sub-parts includes means for associating the name of said list of records which contained the sub-part with the sub-part.

15. A computer programmed according to claim 13 wherein said means for preliminarily grouping said sub-parts into sub-groups comprises:

i) means for comparing each said sub-part to records in said at least one list of records, said at least one list of records also indicating the type of records in the list, and ii) means for representing the sub-part by a related record in said list or by an associated related record if the sub-part matches a record in one of said lists.

16. A computer programmed according to claim 13 wherein said means for completing said sub-groups comprises:

i) means for carrying out a first examination of any sub-parts which may have a dual meaning in order to determine their appropriate meaning in the context of the surrounding sub-parts and inserting associated records from said at least one list of records to alter said sub-part or sub-group, ii) means for examining the sub-groups adjacent each said sub-group in order to extract or copy sub-parts into an incomplete sub-group, and iii) means for carrying out a second examination of sub-parts which may have a dual meaning to determine their appropriate meaning in the context of the surrounding sub-parts and inserting records from said at least one list of records to alter said sub-part or sub-group.

17. A computer programmed according to claim 13 wherein at least one of said at least one list of records comprise terms relating to medical applications, at least one of said at least one list of records comprises anatomical terms relating to common names or descriptions of the bodily structure, at least one of said at least one list of records comprises clinical terms relating to the treatment of patients, and at least one of said at least one list of records comprises terms relating to the position of said anatomical terms.

18. A computer programmed according to claim 12 wherein said divisions are introduced into said data in order to group associated sub-parts together and the positioning of said divisions is determined by one of a predetermined set of reasons and said means for grouping said sub-parts also includes means for keeping a record of the reason for the positioning of divisions between sub-groups and identifying the list in which each sub-part was found.

19. A computer programmed according to claim 12 wherein said divisions are introduced into said data in order to group associated sub-parts together and the positioning of said divisions is determined by one of a predetermined set of reasons and symbolic indicative codes represent said sub-parts and wherein said symbolic indicative codes are stored in a table along with said sub-part type and said reason for the positioning of divisions between said sub-groups.

20. A computer programmed according to claim 12 wherein said computer also includes, for any sub-group which is in error and therefore unable to be completed during said means for completing, means for outputting a message in order that the data corresponding to that incomplete sub-group may be re-input.

21. A computer programmed according to claim 12 wherein said predetermined distribution of sub-part types comprise a clinical sub-part, an anatomical sub-part and a sub-part relating to the position of said anatomical sub-part.

22. A computer programmed according to claim 12 wherein said means for completing said sub-groups includes, for each sub-group, uniformly positioning said sub-parts within each said sub-group to facilitate efficient searching of said representative data wherein only the sub-part at a relevant position within said sub-part need be examined.

* * * * *